United States Patent [19]
Harada et al.

[11] Patent Number: 5,925,777
[45] Date of Patent: Jul. 20, 1999

[54] SCHIFF BASE QUINONE COMPLEXES AND OPTICAL RECORDING MATERIALS COMPRISING THE SAME

[75] Inventors: Toru Harada; Itsuo Fujiwara, both of Kanagawa, Japan

[73] Assignee: Fuji Photo Film Co., Ltd., Kanagawa, Japan

[21] Appl. No.: 08/791,167

[22] Filed: Jan. 30, 1997

[30] Foreign Application Priority Data

Feb. 23, 1996 [JP] Japan ................................. 8-060348
Jul. 16, 1996 [JP] Japan ................................. 8-186448

[51] Int. Cl.$^6$ .............................. C07F 3/04; C07F 3/00; G03G 1/735; D06P 5/00
[52] U.S. Cl. ............................. 556/1; 556/27; 556/182; 534/12; 534/15; 430/341; 8/506; 8/522
[58] Field of Search ................................. 556/1, 27, 182; 534/12, 15; 8/506, 522; 430/341

[56] References Cited

U.S. PATENT DOCUMENTS 5,306,591  4/1994  Larson et al. ........................... 430/115

OTHER PUBLICATIONS

B.G. Maiya et al: Journal of the Chemical Society Dalton Transactions, 1990, pp. 3571–3576, XP002068712.
Chemical Abstracts, vol. 83, No. 22, Dec. 1, 1975, Columbus, Ohio, US; abstract No. 187582v,p. 590; XP002068713 *abstract* & A.Y. Girgis et al: Inorg. Chem., vol. 14, No. 11, 1975, pp. 2724–2727.
Chemical Abstracts, vol. 122, No. 18, May 1, 1995 Columbus, Ohio, US; abstract No. 223258d, p. 692; XP002068714 *abstract* & T. Ren: Inorg. Chim. Acta, vol. 229, No. 1–2, 1995, pp. 195–202.

Vol. 14, No. 11, Nov. 1975, Inorganic Chemistry, pp. 2724–2727.

Vol. 28, No. 24, Nov. 29, 1989, Inorganic Chemistry, pp. 4379–4385.

Vol. 73, No. 7, Jun. 1995, Canadian Journal of Chemistry, pp. 1213–1222.

Vol. 110, No. 6, Mar. 16, 1998, Journal of the American Chemical Society, pp. 1827–1832.

Vol. 116, No. 4, Feb. 23, 1994, Journal of the American Chemical Society, pp. 1388–1394.

*Primary Examiner*—Porfirio Nazario-Gonzalez
*Attorney, Agent, or Firm*—Sughrue, Mion, Zinn, Macpeak & Seas, PLLC

[57] ABSTRACT

Novel Schiff base quinone complexes are provided. They are useful as anti-fading agents and filter dyes. The anti-fading agents are applicable to heat developable photosensitive materials, silver halide photosensitive materials, and optical recording materials.

7 Claims, No Drawings

SCHIFF BASE QUINONE COMPLEXES AND OPTICAL RECORDING MATERIALS COMPRISING THE SAME

BACKGROUND OF THE INVENTION

1. Field of the Invention

This invention relates to novel Schiff base quinone complexes and their use as an anti-fading agent or dye.

2. Prior Art

Schiff base quinone complexes are described in Inorg. Chem., 28, 4379–4385 (1989), ibid., 14, 2724–2727 (1975), Can. J. Chem., 73, 1213–1222 (1995), J. Am. Chem. Soc., 110, 1827–1832 (1988), and ibid., 116, 1388–1394 (1994). The metal atoms used therein are Sn, Pb, Ni, Fe, Cd, Co, Zn, Mn, Mg, V, and Ti, many of which are deleterious to the environment. No reference is made to the utilization of these complexes as an anti-fading agent or dye.

SUMMARY OF THE INVENTION

Therefore, an object of the present invention is to provide a novel Schiff base quinone complex, especially such a complex having coordinated a metal which is not pollutive to the environment. Another object of the present invention is to utilize the complex as an anti-fading agent and dye.

The objects of the present invention are attained by Schiff base quinone complexes of the following general formulae (1a) and (1b).

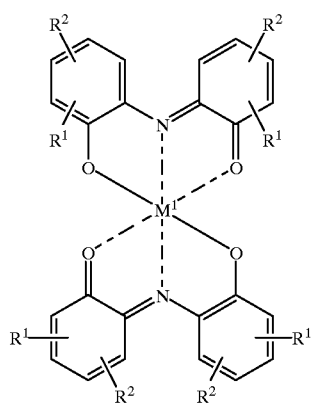

(1a)

In formula (1a), each of $R^1$ and $R^2$ is an alkyl group, and $M^1$ is a metal atom selected from the class consisting of Ca, Ba, Al, Y, In, La, Nd, Sm, Gd, Tb, Dy and Yb.

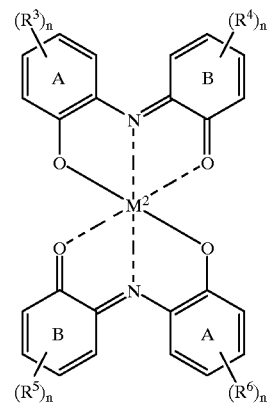

(1b)

In formula (1b), $R^3$, $R^4$, $R^5$, and $R^6$ are independently selected from the class consisting of a hydrogen atom, alkyl group, alkenyl group, alkynyl group, halogen atom, alkoxy group, alkylcarbonyl group, carbamoyl group, acylamino group, alkoxycarbonyl group, and a group of non-metallic atoms necessary to form a hydrocarbon or aromatic ring, rings A and B may be connected directly or through a non-metallic atom, letter n is an integer of 1 to 4, and $M^2$ is a metal atom.

It is noted that the general formula (1b) is alternatively expressed by the following general formula (1b').

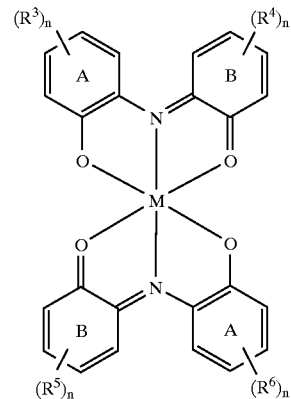

(1b')

DETAILED DESCRIPTION OF THE INVENTION

The general formula (1a) is described in detail.

The alkyl groups represented by $R^1$ and $R^2$ are preferably normal or branched alkyl groups of 1 to 20 carbon atoms, especially 1 to 12 carbon atoms, such as methyl, ethyl, n-butyl, t-butyl, t-pentyl, n-octyl, and t-octyl. More preferred are tertiary branched alkyl groups such as t-butyl, t-pentyl, and t-octyl. Their position of substitution is preferably the ortho- or para-position relative to the carbon atom adjoining the oxygen atom.

$M^1$ is a metal atom Ca, Ba, Al, Y, In, La, Nd, Sm, Gd, Tb, Dy or Yb. Ca and Ba are preferred.

The general formula (1b) is described in detail.

The alkyl groups represented by $R^3$, $R^4$, $R^5$, and $R^6$ are as defined for $R^1$ and $R^2$ in formula (1a).

The halogen atoms represented by $R^3$ to $R^6$ are F, Cl, and Br.

The alkoxy groups represented by $R^3$ to $R^6$ are preferably those of 1 to 16 carbon atoms, such as methoxy and butoxy.

Examples of the alkylcarbonyl group represented by $R^3$ to $R^6$ are ethylcarbonyl, butylcarbonyl, and heptylcarbonyl.

Examples of the alkoxycarbonyl group represented by $R^3$ to $R^6$ are ethoxycarbonyl and butoxycarbonyl.

Examples of the carbamoyl group represented by $R^3$ to $R^6$ are methylcarbamoyl and dodecylcarbamoyl.

Examples of the acylamino group represented by $R^3$ to $R^6$ are acetylamino and lauroylamino.

The rings formed by $R^3$ to $R^6$ include carbon rings (such as cyclohexane and cyclopentane) and aromatic rings (such as benzene and naphthalene), which are preferably fused to the ring A or B.

The rings A and B may be connected directly or through O, S or NH to form a ring, for example, carbazole, acrydine, and phenothiazine.

Letter n is an integer of 1 to 4, preferably equal to 2.

The metal atom represented by $M^2$ includes alkaline earth metals such as Mg, Ca and Ba, transition metals such as Cr, Mn, Fe, Co, Ni, and Cu, lanthanoids such as La, Nd, and Yb, and Zn, Al, and Sn. Among others, Ca, Ba, Fe, Cu, Al, and Zn are preferred, with Ca and Ba being especially preferred.

In one embodiment wherein the compound of the invention is used as an anti-fading agent, it is effective for preventing fading of many dyes including azo, azomethine, benzylidene, styryl, oxonol, cyanine, merocyanine, anthraquinone, and arylmethane dyes. The anti-fading agent is effective especially for cyanine dyes of the general formula (2a) and squarylium dyes of the general formula (3). First, the cyanine dyes of formula (2a) are described.

(2a)

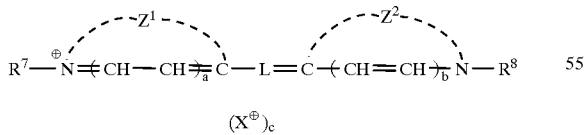

$(X^\ominus)_c$

In formula (2a), each of $Z^1$ and $Z^2$ is a group of nonmetallic atoms necessary to form a five or six-membered nitrogenous heterocyclic ring, which may be a fused one. Each of $R^7$ and $R^8$ is an alkyl, alkenyl or aralkyl group. L is a linkage having 3, 5, 7 or 9 methine groups connected through a conjugated double bond, letters a, b and c each are equal to 0 or 1, and X is an anion.

Examples of the five or six-membered nitrogenous heterocyclic ring, which may be a fused one, represented by $z^1$ and $Z^2$ include oxazole, isooxazole, benzoxazole, naphthoxazole, thiazole, benzothiazole, naphthothiazole, indolenine, benzindolenine, imidazole, benzimidazole, naphthoimidazole, imidazoquinoxaline, quinoline, pyridine, pyrrolopyridine, and furopyrrole rings. The five-membered nitrogenous heterocyclic rings having a benzene or naphthalene ring fused thereto are preferred, with the indolenine ring being most preferred. These rings may be substituted ones. Exemplary substituents include alkyl groups (e.g., methyl and ethyl), alkoxy groups (e.g., methoxy and ethoxy), phenoxy groups (e.g., unsubstituted phenoxy and p-chlorophenoxy), halogen atoms (e.g., Cl, Br, and F), alkoxycarbonyl groups (e.g., ethoxycarbonyl), cyano, nitro, and carboxyl groups. An unsubstituted indolenine ring and substituted indolenine rings having a chloro, methoxy or methyl substituent are especially preferred.

The alkyl groups represented by $R^7$ and $R^8$ are preferably those of 1 to 20 carbon atoms, more preferably 1 to 8 carbon atoms, for example, methyl, ethyl, propyl, butyl, isobutyl, pentyl, and hexyl. They may have substituents, for example, halogen atoms such as F, Cl, and Br, alkoxycarbonyl groups such as methoxycarbonyl and ethoxycarbonyl, and hydroxyl.

The aralkyl groups represented by $R^7$ and $R^8$ are preferably those of 7 to 12 carbon atoms, for example, benzyl and phenylethyl and may have substituents such as methyl, alkoxy and chloro.

The alkenyl groups represented by $R^7$ and $R^8$ are preferably those of 2 to 6 carbon atoms, for example, 2-pentenyl, vinyl, allyl, 2-butenyl, and 1-propenyl.

In formula (2a), L is a linkage having 3, 5, 7 or 9 methine groups connected through a double bond in a conjugated fashion. The number of methine groups is preferably seven (heptamethine compounds).

The methine group may have a substituent although it is preferred that the substituted methine group be a methine group substituted at the center or meso-position. Preferred among the methine groups represented by L are trimethines of the following formula L3, pentamethines of the following formula L5, heptamethines of the following formula L7, and nonamethines of the following formula L9.

(L3)

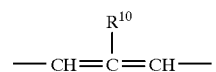

(L5)

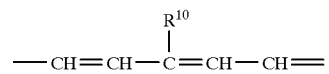

(L7)

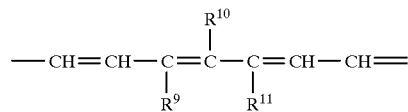

-continued

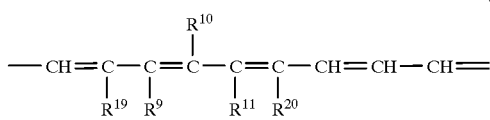

(L9)

In the formulae, $R^{10}$ is a hydrogen atom, alkyl group, halogen atom, aryl group, $NR^{16}R^{17}$, $SR^{18}$ or $OR^{19}$ wherein each of $R^{16}$, $R^{17}$, and $R^{18}$ is an alkyl or aryl group. $R^{16}$ and $R^{17}$, taken together, may form a heterocyclic ring such as piperidine and morpholine. $R^9$ and $R^{11}$ are hydrogen atoms or groups of atoms necessary to form a five or six-membered ring, taken together. Each of $R^{19}$ and $R^{20}$ is a hydrogen atom or alkyl group. Preferably, $R^9$ and $R^{11}$, taken together, form a five or six-membered ring, for example, cyclopentene and cyclohexene rings. These rings may have substituents such as alkyl and aryl groups.

In conjunction with $R^9$, $R^{10}$, $R^{11}$, $R^{19}$, and $R^{20}$, the alkyl groups are the same as defined for $R^7$ and $R^8$. The halogen atoms are F, Cl, and Br. The aryl groups are preferably those of 6 to 12 carbon atoms, for example, phenyl and naphthyl groups. The aryl groups may be either substituted or unsubstituted. Where substituted, exemplary substituents include alkyl groups having up to 10 carbon atoms, preferably up to 6 carbon atoms such as methyl, ethyl, butyl and hexyl, alkoxy groups having up to 10 carbon atoms, preferably up to 6 carbon atoms such as methoxy and ethoxy, aryloxy groups having up to 20 carbon atoms, preferably up to 12 carbon atoms such as phenoxy and p-chlorophenoxy, halogen atoms such as Cl, Br, and F, and alkoxycarbonyl groups having up to 10 carbon atoms, preferably up to 6 carbon atoms such as ethoxycarbonyl as well as cyano, nitro and carboxyl groups.

In formula (2a), letters a, b, and c are equal to 0 or 1. Preferably both a and b are equal to 0 while c is generally equal to 1. It is understood that c is equal to 0 where an anionic substituent such as carboxyl forms an intramolecular salt with $N^+$.

The anions represented by X include halide ions such as Cl, Br and I, p-toluenesulfonate ion, ethylsulfate ion, $PF_6^-$, $BF_4^-$, and $ClO_4^-$.

Cyanine dyes of the general formula (2b) are more preferred.

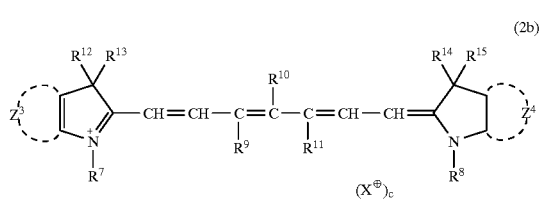

(2b)

In the formula, each of $Z^3$ and $Z^4$ is a group of atoms necessary to form a benzo or naphtho fused ring. Each of $R^7$ and $R^8$ is an alkyl, aralkyl or alkenyl group. Each of $R^9$ and $R^{11}$ is a hydrogen atom or a group of atoms necessary form a five or six-membered ring, taken together. $R^{10}$ is a hydrogen atom, alkyl group, halogen atom, aryl group, $NR^{16}R^{17}$, $SR^{18}$ or $OR^{18}$ wherein each of $R^{16}$, $R^{17}$, and $R^{18}$ is an alkyl or aryl group. $R^{16}$ and $R^{17}$, taken together, may form a five or six-membered ring. Each of $R^{12}$, $R^{13}$, $R^{14}$, and $R^{15}$ is an alkyl group. Alternatively, $R^{12}$ and $R^{13}$, and $R^{14}$ and $R^{15}$, taken together, may form a ring. X is anion. Letter c is equal to 0 or 1.

In formula (2b), the benzo or naphtho fused ring formed by $Z^3$ and $Z^4$ may have a substituent as mentioned for $Z^1$. The alkyl groups represented by $R^7$, $R^8$, $R^{12}$, $R^{13}$, $R^{14}$, $R^{15}$, $R^{16}$, $R^{17}$, and $R^{18}$ are as defined for $R^7$ in formula (2a). $R^{12}$ and $R^{13}$, and $R^{14}$ and $R^{15}$, taken together, may form a ring such as cyclohexane. The alkenyl and aralkyl groups represented by $R^7$ and $R^8$ are the same as the alkenyl and aralkyl groups represented by $R^7$ and $R^8$ in formula (2a). The aryl groups represented by $R^{10}$, $R^{16}$, $R^{17}$, and $R^{18}$ are the same as the aryl groups represented by $R^{10}$ in formula (L5). The halogen atoms represented by $R^{10}$ are the same as the halogen atoms represented by $R^{10}$ in formula (L5). The ring formed by $R^9$ and $R^{11}$ is the same as the ring formed by $R^9$ and $R^{11}$ in formula (L7). The ring formed by $R^{16}$ and $R^{17}$ is the same as the ring formed by $R^{16}$ and $R^{17}$ in formula (L7). X is the same as X in formula (2a). Letter c is the same as c in formula (2a).

Most preferred cyanine dyes are those of formula (2b) wherein each of $R^7$ and $R^8$ is an unsubstituted alkyl group, each of $R^{12}$, $R^{13}$, $R^{14}$, and $R^{15}$ is a methyl group, $R^9$ and $R^{11}$, taken together, form a cyclopentene ring, and $R^{10}$ is a diphenylamino group.

The anti-fading agent of the invention is also effective for squarylium dyes of the following general formula (3):

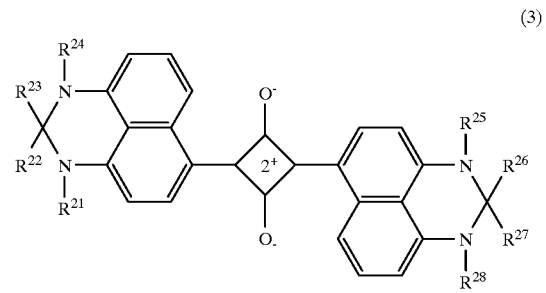

(3)

wherein each of $R^{21}$, $R^{22}$, $R^{23}$, $R^{24}$, $R^{25}$, $R^{26}$, $R^{27}$, and $R^{28}$ is a hydrogen atom, alkyl, cycloalkyl, aryl or aralkyl group. Alternatively, $R^{21}$ and $R^{22}$, $R^{23}$ and $R^{24}$, $R^{25}$ and $R^{26}$, $R^{27}$ and $R^{28}$, $R^{22}$ and $R^{23}$, and $R^{26}$ and $R^{27}$, taken together, may form a five or six-membered ring.

In formula (3), the alkyl and aralkyl groups represented by $R^{21}$ to $R^{28}$ are the same as the alkyl and aralkyl groups represented by $R^7$ in formula (2a). The cycloalkyl group represented by $R^{21}$ to $R^{28}$ includes cyclopentyl and cyclohexyl. The aryl group represented by $R^{21}$ to $R^{28}$ is the same as the aryl group represented by $R^{10}$ in formula (L5).

Examples of the compound of formula (1a) according to the invention are given below as well as examples of the cyanine dye of formula (2a), and the squarylium dyes of formula (3).

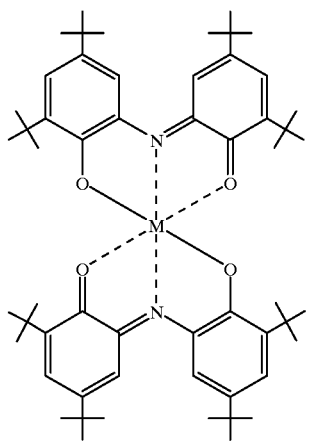
(+ represents tert-$C_4H_9$)
| Compound | M |
|---|---|
| 1-1 | Ni |
| 1-2 | Co |
| 1-3 | Cu |
| 1-4 | Mn |
| 1-5 | Zn |
| 1-6 | Fe |
| 1-7 | Sn |
| 1-8 | Mg |
| 1-9 | Ca |
| 1-10 | Ba |
| 1-11 | Al |
| 1-12 | Y |
| 1-13 | In |
| 1-14 | La |
| 1-15 | Nd |
| 1-16 | Sm |
| 1-17 | Gd |
| 1-18 | Tb |
| 1-19 | Dy |
| 1-20 | Yb |
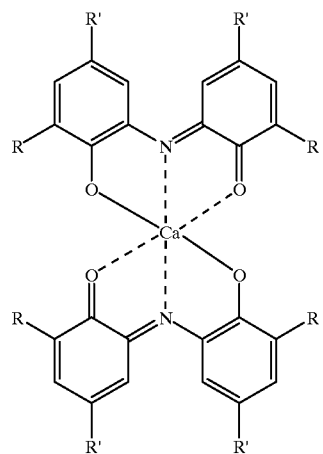
| Compound | R | R' |
|---|---|---|
| 1-21 | t-$C_8H_{17}$ | $CH_3$ |
| 1-22 | $COC_{13}H_{27}$ | $CH_3$ |
| 1-23 | H | t-$C_4H_9$ |
| 1-24 | t-$C_5H_{11}$ | t-$C_5H_{11}$ |

-continued
| | | |
|---|---|---|
| 1-25 | t-C$_8$H$_{17}$ | t-C$_8$H$_{17}$ |
| 1-26 | CO$_2$C$_6$H$_{13}$ | H |
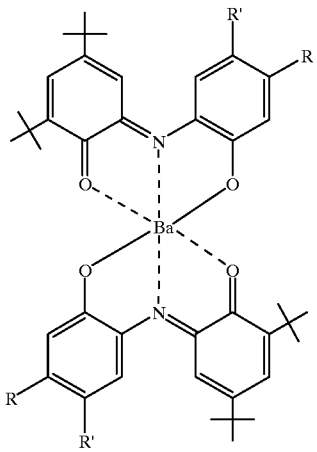
| Compound | R | R' |
|---|---|---|
| 1-27 | NHCOCH$_3$ | H |
| 1-28 | OC$_{16}$H$_{33}$ | H |
| 1-29 | H | CONHC$_{12}$H$_{25}$ |
| 1-30 | CH$_3$ | OC$_{16}$H$_{33}$ |
| 1-31 | OC$_{16}$H$_{33}$ | t-C$_8$H$_{17}$ |
| 1-32 | OC$_{16}$H$_{33}$ | Cl |
Compound 1-33
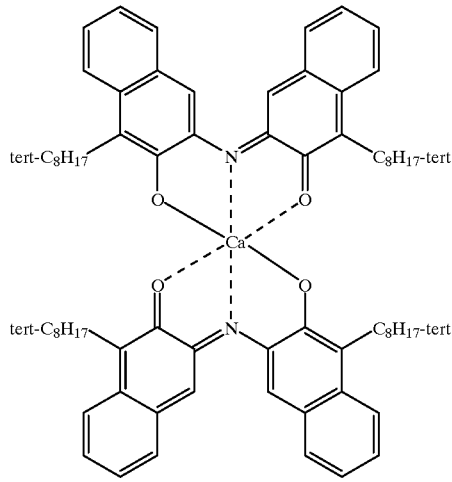

Compound 1-34
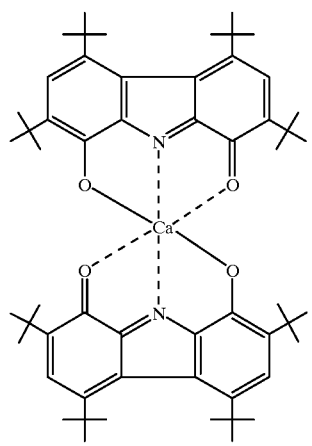
(+ represents t-butyl)
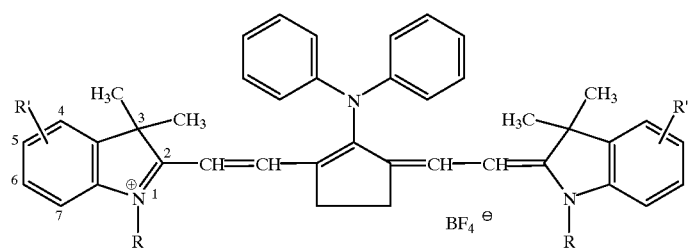
| Compound | R | R' |
|---|---|---|
| 2-1 | —CH₃ | —H |
| 2-2 | —C₄H₉ | 5-Cl |
| 2-3 | —C₆H₁₃ | 5-OCH₃ |
| 2-4 | —C₃H₇ | 5-CN |
| 2-5 | —CH₃ | 5-CO₂C₂H₅ |
| 2-6 | " | 5-NO₂ |
| 2-7 | " | 5-CH₃ |
| 2-8 | " | 5,6-di-Cl |
| 2-9 | " | 4,6-di-Cl |
| 2-10 | —C₂H₅ | 5-Cl |
Under the reading "R'", the preceding number represents the substituting position
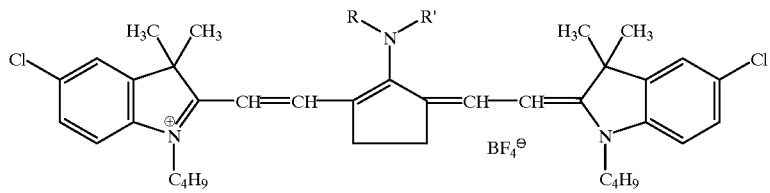
| Compound | R | R' |
|---|---|---|
| 2-11 | —CH₃ |  |
| 2-12 | —C₂H₅ |  |

| | | |
|---|---|---|
| 2-13 | 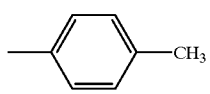 | 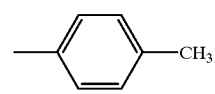 |
| 2-14 | 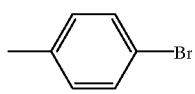 | 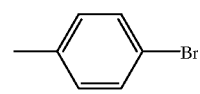 |
| 2-15 | 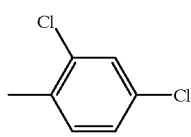 | 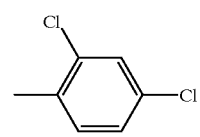 |
| 2-16 | 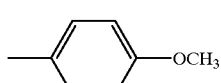 | 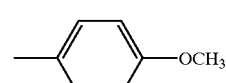 |
| 2-17 | 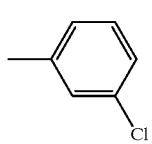 | 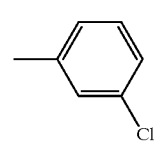 |
| 2-18 | —CH$_3$ | —CH$_3$ |
| 2-19 | —C$_2$H$_5$ | —C$_2$H$_5$ |
| 2-20 | —CH$_2$CO$_2$CH$_3$ | —CH$_2$CO$_2$CH$_3$ |
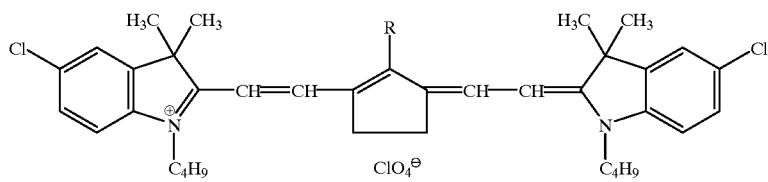
| Compound | R |
|---|---|
| 2-21 | —Cl |
| 2-22 | —OCH$_3$ |
| 2-23 | 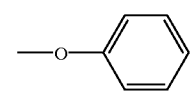 |
| 2-24 | 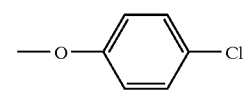 |
| 2-25 | 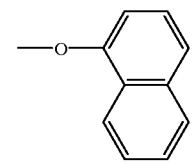 |
| 2-26 | 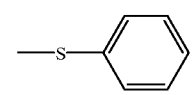 |
| 2-27 | 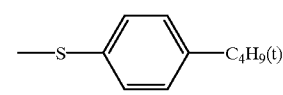 |

2-28 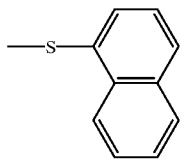
Compound 2-29 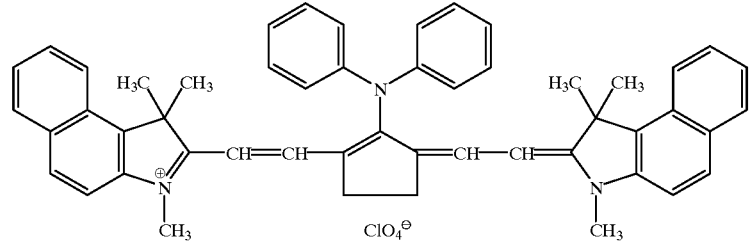
Compound 2-30 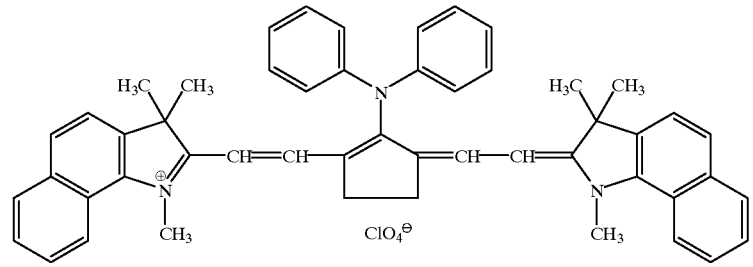
Compound 2-31 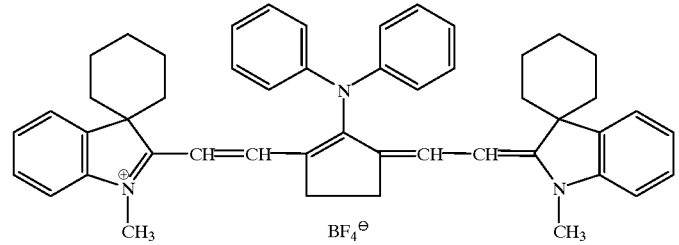
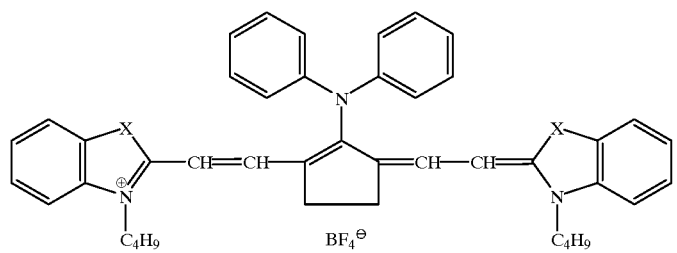
| Compound | X |
|---|---|
| 2-32 | O |
| 2-33 | S |
| 2-34 | N—CH$_3$ |

-continued
Compound 2-35
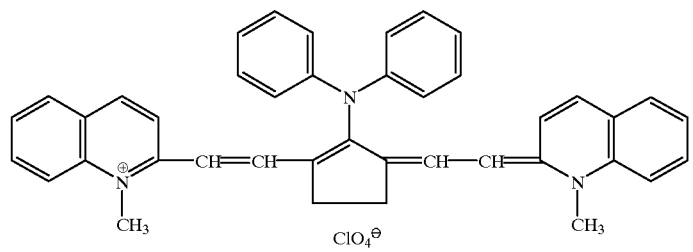
Compound 2-36
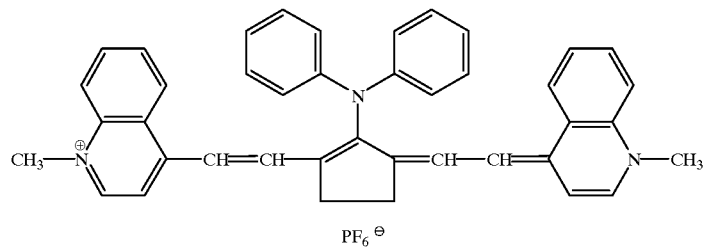
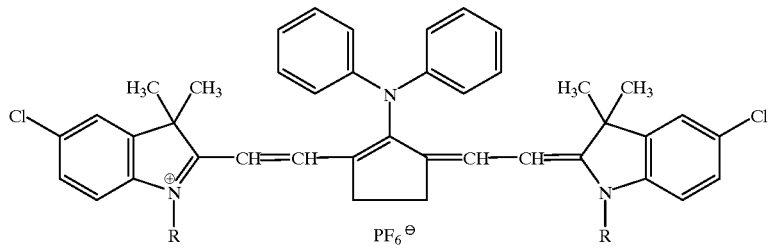
| Compound | R |
|---|---|
| 2-37 | 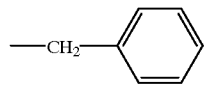 —CH₂— |
| 2-38 | 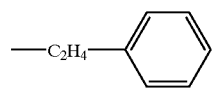 —C₂H₄— |
| 2-39 | —CH₂—CH=CH₂ |
Compound 2-40
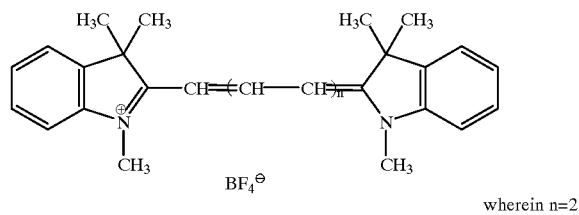
wherein n=2
Compound 2-41  same as 2-40 wherein n = 1
Compound 2-42
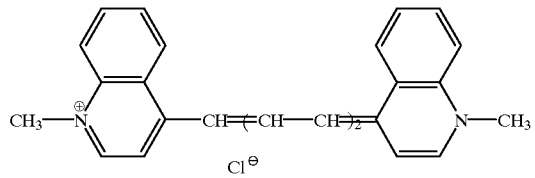

-continued
Compound 2-43 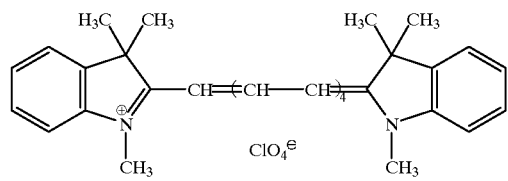
Compound 2-44 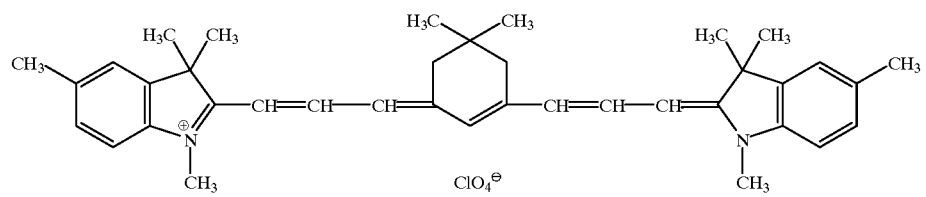
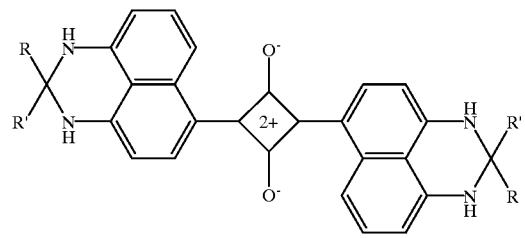
| Compound | R | R' |
|---|---|---|
| 3-1 | $C_2H_5$ | $C_2H_5$ |
| 3-2 | $C_4H_9$ | $C_4H_9$ |
| 3-3 | $CH_3$ | $C_{11}H_{23}$ |
| 3-4 | $CH_3$ | 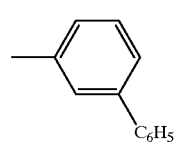 |
| 3-5 | $C_5H_{11}$ | $C_5H_{11}$ |
3-6 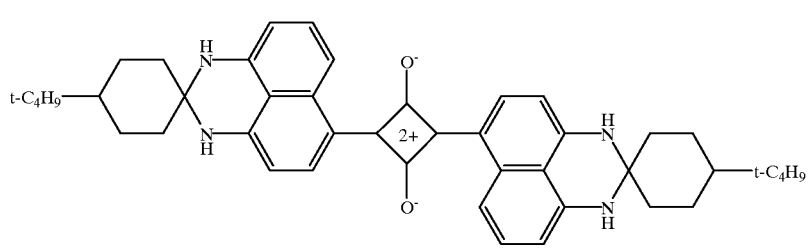
3-7 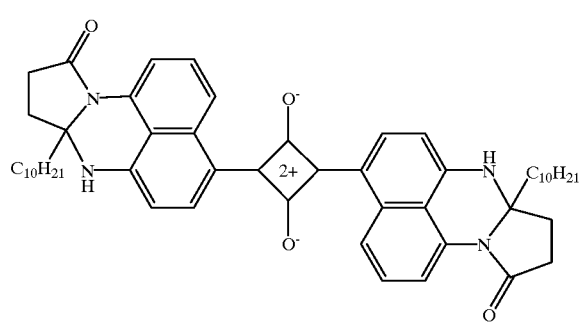

3-8

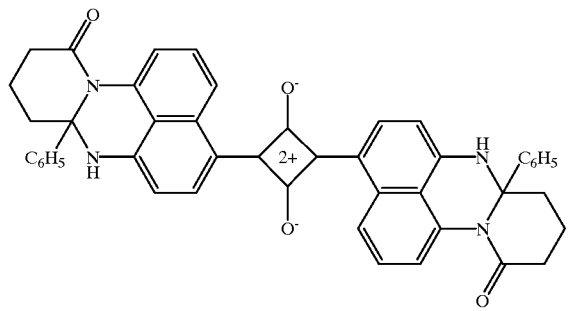

The compounds of general formulae (1a) and (1b) can be obtained by adding a metal salt and ammonia to a solution containing a catechol derivative of the following general formula (4) as will be described in Example.

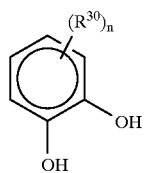

(4)

In formula (4), $R^{30}$ is a hydrogen atom, alkyl group, alkenyl group, alkynyl group, halogen atom, alkoxy group, alkylcarbonyl group, carbamoyl group, acylamino group, alkoxycarbonyl group or a group of non-metallic atoms necessary to form a hydrocarbon or aromatic ring. Letter n is an integer of 1 to 4.

The general formula (4) is described in detail. The alkyl group, alkenyl group, alkynyl group, halogen atom, alkoxy group, alkylcarbonyl group, carbamoyl group, acylamino group, alkoxycarbonyl group or group of non-metallic atoms necessary to form a hydrocarbon or aromatic ring represented by $R^{30}$ are as defined for $R^3$ in formula (1b). Letter n is also as defined in formula (1b).

The catechol derivative is dissolved in a solvent, preferably an organic solvent, for example, methyl alcohol and ethyl alcohol. Examples of the metal salt used herein include salts of divalent metals such as $CaCl_2$, $BaCl_2$, $ZnCl_2$, and NiCl2 and salts of trivalent metals such as $AlCl_3$ and $FeCl_3$. The ammonia used herein is liquid ammonia or aqueous ammonia, with aqueous ammonia being preferred. The metal salt is used in an amount of 0.2 to 0.3 mol, preferably 0.23 to 0.27 mol and ammonia is used in an amount of 3 to 20 mol, preferably 12 to 17 mol per mol of the catechol. Synthesis maybe carried out at a temperature of 10 to 40° C., preferably 20 to 25° C. and accelerated by blowing oxygen or air into the reaction solution.

The compounds of the invention are also useful as a dye which will find photographic anti-halation, medical diagnosis, filter, ink, and paint applications. Use of the inventive compounds as a dye in filter, ink, and paint applications is preferred.

When it is desired to use the inventive compounds in filter, ink, and paint applications, reference is made to Japanese Patent Application Kokai (JP-A) 69686/1989 and 1762/1983. Because of their absorption in the infrared region, the inventive compounds are useful as infrared filters or infrared absorbing ink or paint, which will find use in an invisible bar code system, for example.

Also, the inventive compounds can be used as an anti-fading agent in heat developable photosensitive materials, silver halide photosensitive materials, optical recording materials, pressure and heat sensitive materials, medical diagnostic materials, ink, and paint. Preferably they are used as an anti-fading agent in heat developable photosensitive materials, silver halide photosensitive materials, optical recording materials, ink, and paint.

In the embodiment wherein the inventive compound is used as an anti-fading agent for a dye, the dye and the anti-fading agent are preferably mixed in a weight ratio between 1:0.1 and 1:20, more preferably between 1:0.2 and 1:10, most preferably between 1:0.5 and 1:3.

In heat developable photosensitive material having a photosensitive layer on a support, the anti-fading agent may be added to a dye layer on the same side as the photosensitive layer close to the support and a dye layer remote from the photosensitive layer. The anti-fading agent may be added in an amount of 0.1 to 1,000 $mg/m^2$, preferably 1 to 200 $mg/m^2$ although the amount varies with a particular purpose. Preferably the anti-fading agent is added as a solution in organic solvent. The dye may be added in an amount of 0.1 to 1,000 $mg/m^2$, preferably 1 to 200 $mg/m^2$ in the same layer as the anti-fading agent. Where a binder is used, the dye may be added in an amount of 0.1 to 60% by weight, preferably 0.2 to 30% by weight, more preferably 0.5 to 10% by weight of the binder.

For environmental protection, heat developable photosensitive material is preferably of the type wherein the dye is substantially left on an image sheet to be viewed. More preferred is heat developable photosensitive material of the mono-sheet type wherein all the materials provided for image formation constitute an image sheet to be viewed. For a particular purpose, heat developable photosensitive material adapted for infrared laser exposure is preferred. It is preferred that the infrared laser have a wavelength of at least 750 nm, especially at least 800 nm.

The heat developable photosensitive material according to the invention is to form a photographic image through heat development process. Such heat developable photosensitive materials are disclosed in U.S. Pat. Nos. 3,152,904 and 3,457,075 and D. Morgan and B. Shely, "Thermally Processed Silver Systems" in Imaging Processes and Materials, Neblette, 8-th Ed., Sturge, V. Walworth and A. Shepp Ed., page 2, 1969.

Although the heat developable photosensitive material according to the invention is only required to form a photographic image through heat development process, it preferably contains a reducible silver source (e.g., organic silver salt), a catalytic amount of photocatalyst (e.g., silver halide), a toning agent for controlling the tone of silver, and a reducing agent as dispersed in an organic binder matrix. The heat developable photosensitive material is stable at room temperature and it is developed after exposure by heating at elevated temperatures, for example, 80° C. or higher. Upon heating, redox reaction takes place between the reducible silver source (functioning as an oxidizing agent) and the reducing agent to form silver. The latent image generated by exposure provides catalysis to promote this redox reaction. Reaction of the organic silver salt in the exposed areas generates silver which provides a black image in contrast to the unexposed areas. An image is formed in this way.

The heat developable photosensitive material according to the invention has at least one photosensitive layer on a support. It is acceptable that only a photosensitive layer is formed on a support although it is preferred to form at least one nonphotosensitive layer on the photosensitive layer.

In order to control the quantity or wavelength distribution of light transmitted by the photosensitive layer, a filter layer may be formed on the same or opposite side with respect to the photosensitive layer. The photosensitive layer may contain a dye of formula (2a), (2b) or (3) as well as another dye or pigment. The photosensitive layer may be divided into plural layers while a combination of high sensitivity layer/low sensitivity layer or low sensitivity layer/high sensitivity layer is employable for gradation adjustment. Various additives may be added to any of the photosensitive layer, non-sensitive layer, and other layers.

Various supports are employable in the heat developable photosensitive material according to the invention. Exemplary supports are paper, polyethylene-coated paper, polypropylene-coated paper, parchment, and fabric; sheets or films of metals such as aluminum, copper, magnesium, and zinc; glass and glass coated with metals such as chromium alloy, steel, silver, gold and platinum; and synthetic polymers, for example, poly(alkyl methacrylates) such as poly(methyl methacrylate), polyesters such as poly(ethylene terephthalate, polyvinylacetals, polyamides such as nylon, and cellulose esters such as cellulose nitrate, cellulose acetate, cellulose acetate propionate, and cellulose acetate butyrate.

In the heat developable photosensitive material according to the invention, there may be used surfactants, antioxidants, stabilizers, plasticizers, UV absorbers, coating aids, and the like.

Binder layers, for example, of a synthetic polymer may form self-sustaining films with respective chemicals to be contained in the heat developable photosensitive material according to the invention. The support may be subordinately coated with well-known subordinate materials, for example, vinylidene chloride, acrylic acid monomers such as acrylonitrile and methyl acrylate, unsaturated dicarboxylic acids such as itaconic acid and acrylic acid, carboxymethyl cellulose, copolymers and terpolymers of poly (acrylamide), and analogous polymeric materials.

Preferred binders are transparent or translucent and generally colorless, and include natural polymers, synthetic resins, polymers and copolymers, and other film-forming media, for example, gelatin, gum arabic, poly(vinyl alcohol), hydroxyethyl cellulose, cellulose acetate, cellulose acetate butyrate, poly(vinylpyrrolidone), casein, starch, poly (acrylic acid), poly(methyl methacrylate), polyvinyl chloride, poly(methacrylic acid), styrene-maleic anhydride copolymers, styrene-acrylonitrile copolymers, styrene-butadiene copolymers, poly(vinyl acetals) (e.g., polyvinyl formal and polyvinyl butyral), polyesters, polyurethanes, phenoxy resins, poly(vinylidene chloride), polyepoxides, polycarbonates, poly(vinyl acetate), cellulose esters, and polyamides. A coating of binder may be formed from a solution or emulsion thereof in water or organic solvent.

Addition of color toning agents is quite desirable. Examples of the color toning agent are disclosed in Research Disclosure No. 17029 and include imides such as phthalimide; cyclic imides, pyrazolin-5-ones and quinazolines such as succinimide, 3-phenyl-2-pyrazolin-5-one, 1-phenylurazole, quinazoline, and 2,4-thiazolidinedione; naphthalimides such as N-hydroxy-1,8-naphthalimide; cobalt complexes such as cobalt hexaminetrifluoroacetate; mercaptans such as 3-mercapto-1,2,4-triazole; N-(aminomethyl)aryldicarboxyimides such as N-(dimethylaminomethyl)phthalimide; combinations of a blocked pyrazole, isothiuronium derivative, and optical bleaching agent such as a combination of N,N'-hexamethylene(1-carbamoyl-3,5-dimethylpyrazole), 1,8-(3,6-dioxaoctane)bis-(isothiuroniumtrifluoroacetate), and 2-(tribromomethyl-sulfonyl)benzothiazole); merocyanine dyes such as 3-ethyl-5-((3-ethyl-2-benzothiazolinylidene)-1-methylethylidene)-2-thio-2,4-oxazolidinedione; phthalazinone, phthalazinone derivatives and metals salts of such derivatives such as 4-(1-naphthyl) phthalazinone, 6-chlorophthalazinone, 5,7-dimethyloxyphthalazinone, and 2,3-dihydro-1,4-phthalazinedione; combinations of phthalazinone with a sulfinic acid derivative such as 6-chlorophthalazinone plus sodium benzenesulfinate and 8-methylphthalazinone plus sodium p-trisulfonate; a combination of phthalazine and phthalic acid; combination of phthalazine (inclusive of phthalazine addition products) with at least one of maleic anhydride, phthalic acid, 2,3-naphthalenedicarboxylic acid or o-phenylenic acid derivative and anhydrides thereof (e.g., phthalic acid, 4-methylphthalic acid, 4-nitrophthalic acid, and tetrachlorophthalic anhydride); quinazolinediones, benzoxadine, naphthoxazine derivatives; benzoxadine-2,4-diones such as 1,3-benzoxadine-2,4-dione; pyrimidines and asymmetric triazines such as 2,4-dihydroxypyrimidine, and tetraazapentalene derivatives such as 3,6-dimercapto-1,4-diphenyl-1H,4H-2,3a,5,6a-tetraazapentalene.

The preferred color toning agent is phthalazine of the following formula.

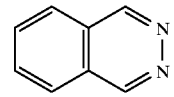

As the reducing agent, so-called photographic developing agents, for example, 1-phenyl-3-pyrazolidone (available as Phenidone®), hydroquinones, and catechols may be contained although hindered phenols are preferred. Also contemplated herein are color photosensitive materials as disclosed in U.S. Pat. No. 4,460,681.

Preferred examples of the reducing agent are disclosed in U.S. Pat. Nos. 3,770,448, 3,773,512, and 3,593,863 and Research Disclosure Nos. 17029 and 29963. Examples include aminohydroxycycloalkenones such as 2-hydroxypiperidino-2-cyclohexenone; amino reductone esters as a precursor of developing agent such as piperidinohexose reductone monoacetate; N-hydroxyurea derivatives such as N-p-methylphenyl-N-hydroxyurea; aldehyde or ketone hydrazones such as anthracenealdehydephenylhydrazone; phosphamidophenols; phosphamidoanilines; polyhydroxybenzenes such as hydroquinone, t-butylhydroquinone, isopropylhydroquinone, and (2,5-dihydroxyphenyl) methylsulfone; sulfohydroxamic acids such as benzenesulfohydroxamic acid; sulfonamidoanilines such as 4-(N-methanesulfonamido)aniline; 2-tetrazolylthiohydroquinones such as 2-methyl-5-(1-phenyl-5-tetrazolylthio)hydroquinone; tetrahydroquinoxalines such as 1,2,3,4-tetrahydroquinoxaline; amidoximes; azines such as combinations of an aliphatic carboxylic acid aryl hydrazide with ascorbic acid; a combination of polyhydroxybenzene with hydroxylamine; reductones and/or hydrazines; hydroxamic acids; combinations of an azine with a sulfonamidophenol; (α-cyanophenylacetic acid derivatives; combinations of bis-β-naphthol with a 1,3-dihydroxybenzene derivative; 5-pyrazolones; sulfonamidophenol reducing agents; 2-phenylindane-1,3-dione; chroman; 1,4-dihydropiridines such as 2,6-dimethoxy-3,5-dicarboethoxy-1,4-dihydropyridine; bisphenols such as bis(2-hydroxy-3-t-butyl-5-methylphenyl)methane, bis(6-hydroxy-m-tri)mesitol, 2,2-bis(4-hydroxy-3-methylphenyl) propane, 4,4-ethylidene-bis(2-t-butyl-6-methyl)phenol, UV-sensitive ascorbic acid derivatives, and 3-pyrazolidones.

Preferred developing agents are hindered phenols of the following general formula (A):

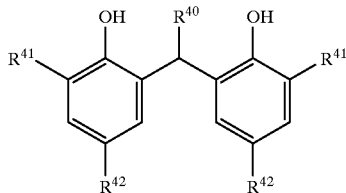

wherein $R^{40}$ is a hydrogen atom or an alkyl group having 1 to 10 carbon atoms such as $-C_4H_9$ and 2,4,4-trimethylpentyl; $R^{41}$ and $R^{42}$ each are an alkyl group having 1 to 5 carbon atoms such as methyl, ethyl, and t-butyl.

The silver halide useful as a catalytic amount of photocatalyst may be any of photosensitive silver halides such as silver bromide, silver iodide, silver chloride, silver chlorobromide, silver iodobromide, and silver chloroiodobromide although inclusion of an iodide ion is preferred. The silver halide may be added to the image-forming layer by any desired method insofar as the silver halide is disposed close to the reducible silver source. In general, the silver halide is ontained in an amount of 0.75 to 30% by weight of the reducible silver source. The silver halide may be prepared by conversion of a silver soap moiety by reaction with a halide ion or preformed and added during generation of a soap. A combination of these techniques is possible and rather preferred.

Any desired material containing a reducible silver ion source may be used as the reducible silver source. Preferred are silver salts of organic acids and hetero-organic acids, especially long-chain aliphatic carboxylic acids (of 10 to 30, preferably 15 to 25 carbon atoms). Also useful are organic or inorganic silver salt complexes wherein the ligand has an overall stability constant of 4.0 to 10.0 relative to silver ion. Preferred examples of the silver salt are described in Research Disclosure Nos. 17029 and 29963 and include salts of organic acids such as gallic acid, oxalic acid, behenic acid, stearic acid, palmitic acid, and lauric acid; silver salts of carboxyalkylthioureas such as 1-(3-carboxypropyl) thiourea and 1-(3-carboxypropyl)-3,3-dimethylthiourea; silver complexes of polymeric reaction products of an aldehyde with a hydroxysubstituted aromatic carboxylic acid (examples of the aldehyde are formaldehyde, acetaldehyde, and butylaldehyde, and examples of the hydroxy-substituted acid are salicylic acid, benzoic acid, 3,5-dihydroxybenzoic acid, and 5,5-thiodisalicylic acid); silver salts or complexes of thioenes such as 3-(2-carboxyethyl)-4-hydroxymethyl-4-thiazoline-2-thioene and 3-carboxymethyl-4-thiazoline-2-thioene; complexes or salts of silver with nitrogenous acids such as imidazole, pyrazole, urazole, 1,2,4-thiazole, 1H-tetrazole, 3-amino-5-benzylthio-1,2,4-triazole, and benzotriazole; silver salts of saccharin, 5-chlorosalicylaldoxime, etc.; and silver salts of mercaptides. The preferred silver source is silver behenate. The reducible silver source is preferably used in an amount of up to 3 g/m² of silver, more preferably up to 2 g/m² of silver.

An antifoggant may be contained in the photosensitive material according to the invention. The most effective antifoggant was mercury ion. Use of a mercury compound as the antifoggant in photosensitive material is disclosed, for example, in U.S. Pat. No. 3,589,903. Mercury compounds, however, are undesirable from the environmental aspect. Preferred in this regard are non-mercury antifoggants as disclosed, for example, in U.S. Pat. Nos. 4,546,075 and 4,452,885 and JP-A 57234/1984.

Especially preferred non-mercury antifoggants are compounds as disclosed in U.S. Pat. Nos. 3,874,946 and 4,756, 999 and heterocyclic compounds having at least one substituent represented by $-C(X^1)(X^2)(X^3)$ wherein $X^1$ and $X^2$ are halogen atoms such as F, Cl, Br, and I, and $X^3$ is hydrogen or halogen. Preferred examples of the antifoggant are shown below.

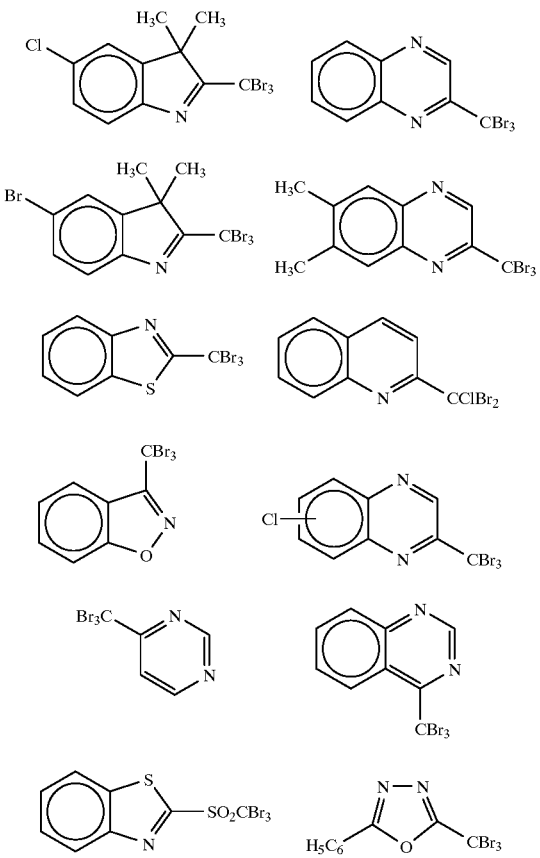

-continued

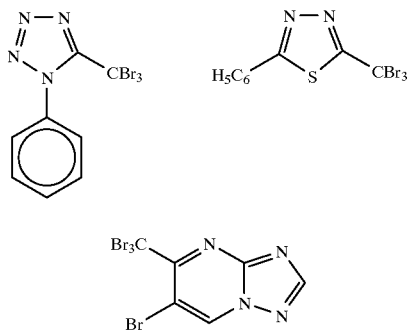

More preferred antifoggants are disclosed in U.S. Pat. No. 5,028,523, British Patent Application Nos. 92221383.4, 9300147.7 and 9311790.1 by the same assignee as the present invention.

In the heat developable photosensitive material according to the invention, there may be used sensitizing dyes as disclosed in JP-A 159841/1988, 140335/1985, 231437/1988, 259651/1988, 304242/1988, and 15245/1988, U.S. Pat. Nos. 4,639,414, 4,740,455, 4,741,966, 4,751,175, and 4,835,096.

The inventive compounds are also applicable to silver halide photosensitive material. With respect to couplers, spectral sensitizers, silver halide emulsions, development promoters, UV absorbers, dyes, hardeners, anti-color mixing agents, surfactants, and other components used in the silver halide photosensitive material, reference is made to JP-A 261350/1995.

The inventive compounds are also applicable to optical recording materials. In this regard, reference is made to JP-A 84383/1990 and 171891/1989.

EXAMPLE

Examples of the present invention are given below by way of illustration and not by way of limitation.

Example 1
Synthesis of compound 1-9

To a solution of 26.7 grams of 3,5-di-t-butylcatechol in 1500 ml of ethyl alcohol were added 250 ml of an aqueous solution containing 3.2 grams of calcium chloride and 125 ml of 25% aqueous ammonia. Air was blown into the reaction solution for 3 hours. The precipitated crystal was then collected by filtration and recrystallized from chloroform, yielding 18 grams of compound 1-9.

m.p.: 262–265° C.; $\lambda$max: 743.4 nm ($CH_2Cl_2$); $\epsilon$: 3.47× $10^4$; Elemental analysis:

|   | Calcd. | Found (2 times) | |
|---|---|---|---|
| C | 75.96% | 75.65% | 74.77% |
| H | 9.11 | 9.30 | 9.05 |
| N | 3.16 | 3.09 | 3.04 |

Synthesis of compound 1-10

To a solution of 5.3 grams of 3,5-di-t-butylcatechol in 300 ml of ethyl alcohol were added 50 ml of an aqueous solution containing 1.4 grams of barium chloride dihydrate and 25 ml of 25% aqueous ammonia. The reaction solution was agitated at room temperature for 5 hours. The precipitated crystal was then collected by filtration and recrystallized from chloroform and methyl alcohol, yielding 3 grams of compound 1-10.

m.p.: 212–217° C. or higher; $\lambda$max: 748.4 nm ($CH_2Cl_2$); $\epsilon$: 2.36×$10^4$; Elemental analysis:

|   | Calcd. | Found (2 times) | |
|---|---|---|---|
| C | 68.46% | 68.10% | 68.22% |
| H | 8.21 | 8.30 | 8.12 |
| N | 2.85 | 2.80 | 2.78 |

Other compounds could be similarly synthesized. Table 1 shows the melting point and spectral data of compounds synthesized under similar conditions. The spectral data indicate peaks in ultraviolet to infrared regions as measured in dichloromethane. Values of elemental analysis were well coincident with the calculated values.

TABLE 1

| Compound | m.p. | $\lambda$max$^1$ | $\lambda$max$^2$ | $\lambda$max$^3$ | $\lambda$max$^4$ | $\lambda$max$^5$ | $\lambda$max$^6$ | $\lambda$max$^7$ |
|---|---|---|---|---|---|---|---|---|
|  |  | (lower row shows $\epsilon$ × $10^{-4}$, $M^{-1}cm^{-1}$) | | | | | | |
| 1-1 | >300 | 836 nm | 766 nm | 430 nm | | | | |
|  |  | 2.69 | 2.89 | 1.80 | | | | |
| 1-2 | 290–297 | 1015 | 784 | 700 | 520 | | | |
|  |  | 0.54 | 1.11 | 0.96 | 0.87 | | | |
| 1-3 | 227–230 | 850 | 762 | 436 | 330 | | | |
|  |  | 2.20 | 2.78 | 1.15 | 0.76 | | | |
| 1-4 | 290–298 | 1250 | 1075 | 890 | 800 | 580 | 476 | 453 |
|  |  | 0.33 | 0.40 | 0.87 | 0.79 | 0.96 | 1.17 | 1.18 |
| 1-5 | 270–280 | 800 | 732 | 430 | 364 | | | |
|  |  | 2.95 | 3.43 | 0.86 | 0.70 | | | |
| 1-6 | 278–285 | 850 | 450 | 354 | | | | |
|  |  | 1.58 | 1.24 | 1.58 | | | | |
| 1-7 | >300 | 1000 | 563 | | | | | |
|  |  | 1.43 | 0.61 | | | | | |
| 1-8 | >300 | 795 | 724 | 432 | | | | |
|  |  | 3.91 | 4.31 | 1.16 | | | | |
| 1-9 | 262–265 | 743 | 441 | 342 | | | | |
|  |  | 3.47 | 0.63 | 0.90 | | | | |
| 1-10 | 212–217 | 783 | 541 | 449 | 338 | | | |
|  |  | 2.36 | 0.81 | 0.70 | 0.85 | | | |
| 1-11 | >300 | 950 | 764 | 532 | 454 | 393 | | |
|  |  | 1.11 | 1.71 | 0.47 | 1.23 | 3.56 | | |

TABLE 1-continued

| Compound | m.p. | λmax¹ | λmax² | λmax³ | λmax⁴ | λmax⁵ | λmax⁶ | λmax⁷ |
|---|---|---|---|---|---|---|---|---|
| | | (lower row shows $\epsilon \times 10^{-4}$, $M^{-1}cm^{-1}$) | | | | | | |
| 1-12 | >300 | 820 | 743 | 532 | 444 | 380 | | |
| | | 4.30 | 4.66 | 0.79 | 1.13 | 1.31 | | |
| 1-13 | 236–240 | 820 | 726 | 536 | 440 | 392 | | |
| | | 2.19 | 2.58 | 0.52 | 0.68 | 0.95 | | |
| 1-14 | >300 | 820 | 766 | 536 | 448 | 392 | 338 | |
| | | 4.67 | 4.70 | 0.68 | 0.91 | 0.73 | 1.27 | |
| 1-15 | >300 | 822 | 760 | 536 | 448 | 392 | 336 | |
| | | 4.62 | 4.71 | 0.72 | 0.99 | 0.78 | 1.27 | |
| 1-16 | >300 | 820 | 756 | 540 | 444 | 390 | 334 | |
| | | 4.68 | 4.86 | 0.75 | 1.05 | 0.81 | 1.31 | |
| 1-17 | >300 | 820 | 750 | 536 | 444 | 388 | 334 | |
| | | 4.78 | 5.06 | 0.80 | 1.13 | 0.87 | 1.41 | |
| 1-18 | >300 | 820 | 750 | 530 | 444 | 384 | 332 | |
| | | 3.91 | 4.19 | 0.70 | 1.03 | 0.74 | 1.16 | |
| 1-19 | >300 | 820 | 748 | 532 | 442 | 380 | 334 | |
| | | 4.39 | 4.70 | 0.77 | 1.11 | 0.87 | 1.29 | |
| 1-20 | >300 | 820 | 744 | 536 | 442 | 380 | 334 | |
| | | 4.51 | 4.85 | 0.86 | 1.24 | 0.94 | 1.39 | |

Example 2 (Filter use)

Sample (001) was prepared by coating layers of the following compositions to a triacetyl cellulose film support having an undercoat layer.

| (1) Filter layer | |
|---|---|
| Compound 1-9 | 0.2 g/m² |
| Tricresyl phosphate | 1.0 g/m² |
| Gelatin | 3.8 g/m² |
| (2) Protective layer | |
| Sodium 2,4-dichloro-6-hydroxy-s-triazine | 0.1 g/m² |
| Gelatin | 1.8 g/m² |

Samples (002) to (005) were similarly prepared except that compound 1-9 in sample (001) was replaced by an equimolar amount of other inventive compounds or a comparative compound.

Each sample was divided into two sections. One section was allowed to stand at 60° C. and RH 70% for 10 days. The other section was exposed to a fluorescent lamp of 20,000 lux for 5 days. After the fade tests, the sections were measured for a residual dye concentration. A percent retention of the dye was calculated as the residual dye concentration divided by the initial dye concentration. The results are shown in Table 2.

compound a

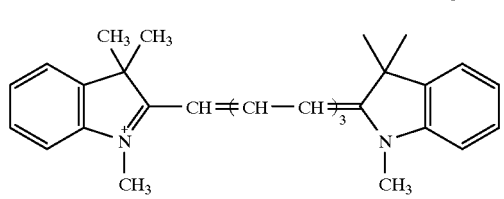

TABLE 2

| Sample No. | Compound | Dye retention after hot, humid fading test | Dye retention after light exposure fading test | Remarks |
|---|---|---|---|---|
| 001 | 1-9 | 99% | 98% | Invention |
| 002 | 1-10 | 98% | 97% | Invention |
| 003 | 1-5 | 99% | 98% | Invention |
| 004 | 1-6 | 97% | 97% | Invention |
| 005 | compound (a) | 60% | 20% | Comparison |

It is evident that the inventive compounds are stable. The calcium and barium complexes are favorable from the environmental aspect since they are less toxic.

Example 3 (Heat developable photosensitive material) Preparation of photosensitive emulsion A

| Solution (1) | | |
|---|---|---|
| Stearic acid | 131 | g |
| Behenic acid | 635 | g |
| Distilled water | 13 | liters |
| mixing at 85° C. for 15 minutes | | |
| Solution (2) | | |
| NaOH | 89 | g |
| Distilled water | 1500 | ml |
| Solution (3) | | |
| Conc. HNO₃ | 19 | ml |
| Distilled water | 50 | ml |
| Solution (4) | | |
| AgNO₃ | 365 | g |
| Distilled water | 2500 | ml |
| Solution (5) | | |
| Polyvinyl butyral | 86 | g |
| Ethyl acetate | 4300 | ml |
| Solution (6) | | |
| Polyvinyl butyral | 290 | g |
| Isopropanol | 3580 | ml |

-continued

Solution (7)

| | |
|---|---|
| N-bromosuccinimide | 9.7 g |
| Acetone | 690 ml |

With vigorous stirring, solution (2) was added over 5 minutes to solution (1) kept at 85° C., and solution (3) was then added over 25 minutes. Stirring was continued for a further 20 minutes and then the temperature was lowered to 35° C. With more vigorous stirring at 35° C., solution (4) was added over 5 minutes, and stirring was continued for a further 90 minutes. Then solution (5) was added, stirring was interrupted, and the reaction solution was allowed to stand. The aqueous phase was removed together with the salts contained therein, collecting an oil phase. The solvent was removed from the oil phase and a trace of water was removed. Solution (6) was added to the residue, which was vigorously stirred at 50° C. Solution (7) was added over 20 minutes. Stirring for a further 105 minutes yielded emulsion A.

On a polyethylene terephthalate support tinted blue with dye-A, the following layers were successively formed. Each coating step was followed by drying at 75° C. for 5 minutes.

Back surface side coating

Anti-halation layer (wet thickness 80 microns)

| | | |
|---|---|---|
| 1:1 mixture of polyvinyl butyral (10% isopropanol solution) and cellulose acetate butyrate (10% isopropanol solution) | 150 | ml |
| Dye (DMF, acetone or methyl chloride was used as solvent) | 42 | mg |
| Anti-fading agent (ethyl acetate or methyl chloride was used as solvent) | 45 | mg |

Photosensitive layer side coating

Photosensitive layer (wet thickness 140 microns)

| | | |
|---|---|---|
| Photosensitive emulsion A | 73 | g |
| Sensitizing dye-1 (0.1% DMF solution) | 2 | ml |
| Antifoggant-1 (0.01% methanol solution) | 3 | ml |
| Antifoggant-2 (0.85% methanol solution) | 10 | ml |
| Antifoggant-3 (0.85% methanol solution) | 10 | ml |
| Phthalazone (4.5% DMF solution) | 8 | ml |
| Reducing agent-1 (10% acetone solution) | 13 | ml |

Surface protective layer (wet thickness 100 microns)

| | | |
|---|---|---|
| Acetone | 175 | ml |
| 2-propanol | 40 | ml |
| Methanol | 15 | ml |
| Cellulose acetate | 8.0 | g |
| Phthalazine | 1.0 | g |
| 4-methylphthalic acid | 0.72 | g |
| Tetrachlorophthalic acid | 0.22 | g |
| Tetrachlorophthalic anhydride | 0.5 | g |

Sensitizing dye-1

Antifoggant-1

Antifoggant-2 (described in USP 3,874,946)

Antifoggant-3 (described in EP 605981)

Reducing agent-1

Dye-A

Sensitometry

The thus prepared heat developable photosensitive material was cut into sections of folio size and exposed to a beam of 830 nm emitted from a laser diode at an angle of 13° with respect to a normal plane. Using a heat drum, heat development was then carried out at 120° C. for 5 seconds.

Sharpness rating

The photosensitive material sample was exposed to light of 830 nm spectrally selected from white light of 2856K through an interference filter, processed under the above-mentioned conditions, and rated for sharpness in terms of an MTF value at 15 lines/mm at an optical density of 1.0.

Color rating

The photosensitive material sample was heat developed without exposure. It was visually observed and rated "O" for good, "Δ" for noticeable color, and "X" for poor color.

Light-fastness rating

Using a xenon lamp illuminating equipment (lamp: Xenon Burner Warranty Log Wattage 3500/6500 type) by Atlas Electric Device, the photosensitive material sample on the backcoating side was subject toalighting cycle of lighting (8500 1x/30° C./30% RH/3.8 hours) and turning off (20° C./90% RH/1 hour) 5 rounds for a total time of 24 hours. A percent retention of the dye was determined from a change of absorption spectrum.

TABLE 3

| No. | Dye | Anti-fading agent | Color | Sharpness MTF | Retention (%) |
|---|---|---|---|---|---|
| 101* | — | — | O | 0.56 | — |
| 102* | 2-7 | — | O | 0.92 | 12 |
| 103 | 2-7 | 1-5 | O | 0.93 | 68 |
| 104 | 2-7 | 1-6 | O | 0.94 | 85 |
| 105 | 2-7 | 1-9 | O | 0.94 | 70 |
| 106 | 2-7 | 1-10 | O | 0.92 | 54 |
| 107* | 2-10 | — | O | 0.93 | 10 |
| 108 | 2-10 | 1-9 | O | 0.93 | 71 |
| 109 | 2-10 | 1-10 | O | 0.94 | 57 |

*comparison

It is evident from Table 3 that samples within the scope of the invention had high sharpness and light fastness and were free of a residual color problem.

Example 4

Preparation of photosensitive emulsion B

| Solution (1) | | |
|---|---|---|
| Stearic acid | 131 | g |
| Behenic acid | 635 | g |
| Distilled water | 13 | liters |
| mixing at 85° C. for 15 minutes | | |
| Solution (A) | | |
| Previously prepared cubic AgBrI | (0.22 | mol Ag) |
| (I = 4 mol %: 0.06 μ) | | |
| Distilled water | 1250 | ml |

-continued

| Solution (2) | | |
|---|---|---|
| NaOH | 89 | g |
| Distilled water | 1500 | ml |
| Solution (3) | | |
| Conc. HNO$_3$ | 19 | ml |
| Distilled water | 50 | ml |
| Solution (4) | | |
| AgNO$_3$ | 365 | g |
| Distilled water | 2500 | ml |
| Solution (5) | | |
| Polyvinyl butyral | 86 | g |
| Ethyl acetate | 4300 | ml |

-continued

| Solution (6) | | |
|---|---|---|
| Polyvinyl butyral | 290 | g |
| Isopropanol | 3580 | ml |

With vigorous stirring, solution (A) was added over 10 minutes to solution (1) kept at 85° C., solution (2) was successively added over 5 minutes, and solution (3) was then added over 25 minutes. Stirring was continued for a further 20 minutes and then the temperature was lowered to 35° C. With more vigorous stirring at 35° C., solution (4) was added over 5 minutes, and stirring was continued for a further 90 minutes. Then solution (5) was added, stirring was interrupted, and the reaction solution was allowed to stand. The aqueous phase was removed together with the salts contained therein, collecting an oil phase. The solvent was removed from the oil phase and a trace of water was removed. Solution (6) was added to the residue, which was vigorously stirred at 50° C. Stirring for a further 105 minutes yielded emulsion B.

Samples were prepared as in Example 3 except that an anti-halation layer was provided under the photosensitive layer on the photosensitive layer side. They were tested as in Example 3.

Samples using anti-fading agents within the scope of the invention had high sharpness and light fastness and were free of a residual color problem.

EXAMPLE 5

An emulsified dispersion was prepared by weighing 9.8 g of cyan coupler (C-1), adding 11.5 g of high-boiling organic solvent tricresyl phosphate thereto, adding 24 ml of ethyl acetate thereto to form a solution, and emulsifying and dispersing the solution in 200 g of a 10 wt % gelatin aqueous solution containing 1.5 g of sodium dodecylbenzene-sulfonate.

Cyan coupler (C-1)

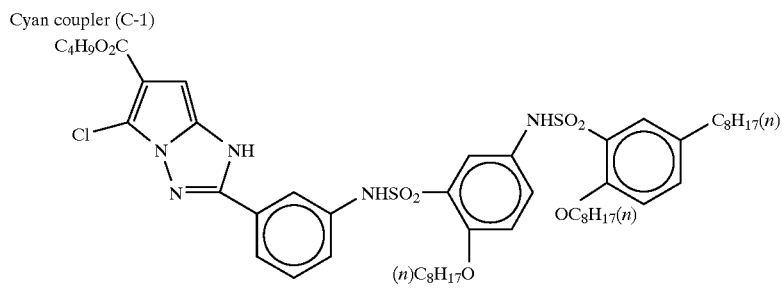

The emulsified dispersion was entirely added to 247 g of a high silver chloride emulsion (silver 70.0 g/kg emulsion, silver bromide content 0.5 mol %). On a triacetate film base having an undercoat layer previously applied at a silver coverage of 1.73 g/m$^2$, the emulsion was coated. On this coating, a gelatin layer was formed as a protective layer to a dry thickness of 1.0 μm, obtaining sample No. 201. The gelatin hardener used herein was a sodium salt of 1-oxy-3,5-dichloro-sec-triazine.

Sample Nos. 202 to 205 were prepared by the same procedure as sample No.201 except that during preparation of the emulsified dispersion, an anti-fading agent as shown in Table 4 was added for co-emulsification in an amount of 100 mol % based on the coupler.

The thus obtained samples were wedge exposed and developed in accordance with the following steps.

| Step | Temperature | Time |
|---|---|---|
| Color development | 35° C. | 45 sec. |
| Bleach fixing | 30–35° C. | 45 sec. |
| Rinse (1) | 30–35° C. | 20 sec. |
| Rinse (2) | 30–35° C. | 20 sec. |
| Rinse (3) | 30–35° C. | 20 sec. |
| Drying | 70–80° C. | 60 sec. |

The processing solutions used in these steps are shown below.

| Color developer | | |
|---|---|---|
| Water | 800 | ml |
| Ethylenediamine-N,N,N',N'-tetramethylenesulfonic acid | 1.5 | g |
| Potassium bromide | 0.015 | g |
| Triethanolamine | 8.0 | g |
| Sodium chloride | 1.4 | g |
| Potassium carbonate | 25 | g |
| N-ethyl-N-(β-methanesulfonamidoethyl)-3-methyl-4-aminoaniline hydrogen sulfate | 5.0 | g |
| Disodium N,N-bis(sulfonatoethyl)hydroxylamine | 5.5 | g |
| Brightening agent (WHITEX 4B, Sumitomo Chemicals K.K.) | 1.0 | g |
| Water totaling to | 1000 | ml |
| pH (25° C.) | 10.05 | |

| -continued | | |
|---|---|---|
| Bleach fixer | | |
| Water | 400 | ml |
| Ammonium thiosulfate (700 g/liter) | 100 | ml |
| Sodium sulfite | 17 | g |
| Iron (III) ethylenediaminetetraacetate ammonium | 55 | g |
| Disodium iron ethylenediaminetetraacetate | 5 | g |
| Ammonium bromide | 40 | g |
| Water totaling to | 1000 | ml |
| pH (25° C.) | 6.0 | |

Rinse solution

Deionized water containing less than 3 ppm of calcium and magnesium

Sample Nos. 201 to 205 in which dye images were formed in this way were exposed to light for 8 days by means of a xenon tester (illuminance 200,000 lux) equipped with a UV absorbing filter for cutting off light of 400 nm or less (manufactured by Fuji Photo-Film Co., Ltd.). For each sample, a percent retention of density was determined provided that the initial density was 1.0. Measurement was done by means of an automatic recording densitometer manufactured by Fuji Photo-Film Co., Ltd. The results are shown in Table 4.

TABLE 4

| Sample | Anti-fading agent | Retention | Remarks |
|---|---|---|---|
| 201 | — | 45% | Comparison |
| 202 | 1-5 | 92% | Invention |
| 203 | 1-6 | 95% | Invention |
| 204 | 1-9 | 90% | Invention |
| 205 | 1-10 | 91% | Invention |

Additionally, samples were prepared in accordance with Examples 1, 2 and 5 of JP-A 261350/1995 and similarly tested to find that the anti-fading agents within the scope of the invention were fully effective.

Example 6

A dye layer-coating solution was prepared by dissolving 2.0 of cyanine dye (CY-1) in 100 cc of 2,2,3,3-tetrafluoropropanol structural formula: $HCF_2CF_2CH_2OH$).

Cyanine dye (CY-1)

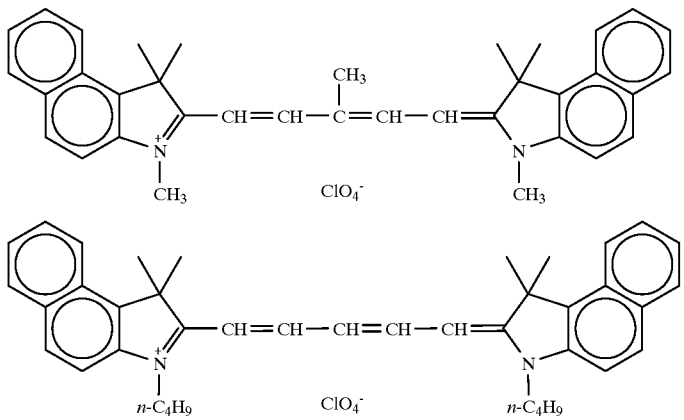

On a disc-shaped polycarbonate substrate having a tracking guide (outer diameter 120 mm, inner diameter 15 mm, thickness 1.2 mm, track pitch 1.6 μm, groove width 0.5 μm, groove depth 900 Å), the coating solution was applied by spin coating at a speed of 1,000 rpm and dried for 30 seconds, forming a recording layer of 2,000 Å thick.

On the recording layer, gold was DC sputtered to form a reflecting layer of 1,300 Å thick. On the reflecting layer, UV curable resin (trade name: 3070, Three Bond Co.) was applied by spin coating at a speed of 1,500 rpm and cured by illuminating ultraviolet radiation from a high pressure mercury lamp, forming a protective layer of 3 μm thick.

In this way, there was prepared an information recording medium (sample No. 301) having a recording layer, reflecting layer and protective layer on a substrate.

Recording media, Nos. 302 to 305, were prepared by the same procedure as No. 301 except that an equimolar amount of an anti-fading agent as shown in Table 5 was added to cyanine dye (CY-1).

Evaluation of information recording media

1) C/N

By passing a semiconductor laser beam having a wavelength of 780 nm through an objective lens with NA=0.5, focusing the beam at the recording layer of the medium, and causing the beam to track the groove, signals of modulated frequency of 720 kHz (duty factor 33%) were recorded in the information recording medium at a constant linear velocity of 1.3 m/sec. and a recording power of 7.0 mW. The recorded signals were read at a reading power of 0.5 mW while a C/N ratio was measured using a spectral analyzer TR4135 (Advantest Co.).

2) Reflectance

Using the same optical system as used in the measurement of C/N, the unrecorded groove was tracked with a laser beam at a reading power of 0.5 mW. The quantity (X) of light reflected back from the medium was measured by a photodetector. With the medium removed, the quantity (Y) of incident light at the position where the medium had been was measured by the same photodetector. A reflectance was calculated as X/Y x 100%.

3) Light fastness

Light fastness was rated by the same procedure as in Example 5 except that a sample was exposed to light at 100,000 lux for 20 hours.

The anti-fading agents added to the dye layer-coating solution in comparative and inventive samples are reported in Table 5 together with the test results.

TABLE 5

| Sample | Anti-fading agent | Groove depth (Å) | Reflectance (%) | C/N (dB) | Retention (%) | Remarks |
|---|---|---|---|---|---|---|
| 301 | — | 900 | 81 | 52 | 42 | Comparison |
| 302 | 1-5 | 900 | 80 | 51 | 78 | Invention |
| 303 | 1-6 | 900 | 79 | 50 | 82 | Invention |
| 304 | 1-9 | 900 | 80 | 51 | 75 | Invention |
| 305 | 1-10 | 900 | 79 | 51 | 80 | Invention |

It is evident from Table 5 that information recording media having a specific recording layer according to the invention had high reflectance and C/N and were fully lightfast.

Example 7 (Ink)

| Compound 1-9 | 5% |
|---|---|
| Ethanol | 20% |
| Ethylene glycol | 20% |
| Distilled water | 55% |

Ink was prepared by agitating the above ingredients at room temperature for one hour. The ink was found useful in an invisible bar code system.

There have been described novel complexes which are effective as an anti-fading agent for preventing recording materials from fading. The inventive compounds are also useful as a filter dye and remain fully stable in such use. Calcium and barium complexes are less toxic and thus favorable from the environmental aspect.

While the invention has been described in what is presently considered to be a preferred embodiment, other variations and modifications will become apparent to those skilled in the art. It is intended, therefore, that the invention not be limited to the illustrative embodiments, but be interpreted within the full spirit and scope of the appended claims.

we claim:

1. A Schiff base quinone complex of the following general formula (1a):

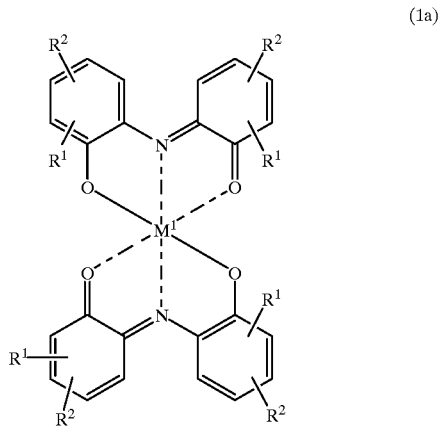

(1a)

wherein each of $R^1$ and $R^2$ is an alkyl group, and $M^1$ is a metal atom selected from the group consisting of Ca, Ba, Y, La, Nd, Sm, Gd, Tb, Dy and Yb.

2. A Schiff base quinone complex according to claim 1 wherein $M^1$ is Ca or Ba.

3. A method for preventing fading comprising adding a compound of formula (1b):

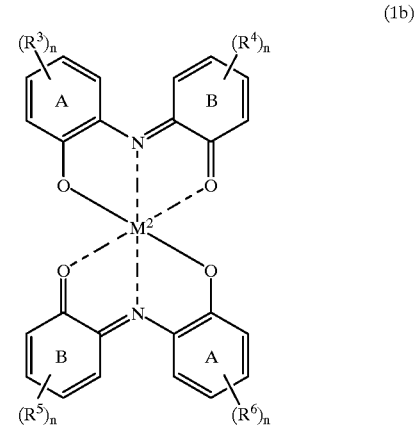

(1b)

to a member selected from the group consisting of heat developable photosensitive materials, silver halide photosensitive materials, silver halide photosensitive materials, optical recording materials, medical diagnostic materials, ink and paint;

wherein, $R^3$, $R^4$, $R^5$, and $R^6$ are independently selected from the group consisting of hydrogen, halogen, alkyl, alkenyl, alkynyl, alkoxy, alkylcarbonyl, carbamoyl, acylamino, alkoxycarbonyl group, and a group of non-metallic atoms necessary to form a hydrocarbon or aromatic ring, rings A and B may be connected directly or through a non-metallic atom, letter n is an integer of 1 to 4, and $M^2$ is a metal atom selected from the group consisting of Ca, Ba, Y, La, Nd, Sm, Gd, Tb, Dy and Yb.

4. The method for preventing fading according to claim 3, wherein said metal atom is Ca or Ba.

5. A method for dyeing comprising adding a compound of formula (1b):

(1b) 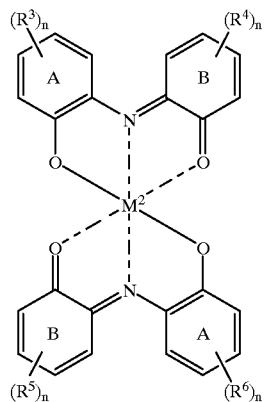

to a member of the group consisting of photographic antihalation materials, medical diagnostic materials, filters, ink and paint;

wherein $R^3$, $R^4$, $R^5$, and $R^6$ are independently selected from the group consisting of hydrogen, halogen, alkyl, alkenyl, alkynyl, alkoxy, alkycarbonyl carbamoyl, acylamino, alkoxycarbonyl group, and a group of non-metallic atoms necessary to form a hydrocarbon or aromatic ring, rings A and B may be connected directly or through a non-metallic atom, letter n is an integer of 1 to 4, and $M^2$ is a metal atom.

6. The method for dyeing according to claim 5, wherein said metal atom is selected from the group consisting of Ca, Ba, Al, Y, In, La, Nd, Sm, Gd, Tb, Dy and Yb.

7. The method for dyeing according to claim 5, wherein said metal atom is Ca or Ba.

* * * * *